US007745190B2

(12) United States Patent
Shimada et al.

(10) Patent No.: US 7,745,190 B2
(45) Date of Patent: Jun. 29, 2010

(54) ENDORIBONUCLEASE

(75) Inventors: Masamitsu Shimada, Shiga (JP);
Masanori Takayama, Shiga (JP);
Kiyoza Asada, Shiga (JP); Ikunoshin Kato, Shiga (JP)

(73) Assignee: Takara Bio Inc., Shiga (JP)

( * ) Notice: Subject to any disclaimer, the term of this patent is extended or adjusted under 35 U.S.C. 154(b) by 15 days.

(21) Appl. No.: 12/067,769

(22) PCT Filed: Sep. 8, 2006

(86) PCT No.: PCT/JP2006/317858

§ 371 (c)(1),
(2), (4) Date: Mar. 21, 2008

(87) PCT Pub. No.: WO2007/034693

PCT Pub. Date: Mar. 29, 2007

(65) Prior Publication Data

US 2009/0047709 A1    Feb. 19, 2009

(30) Foreign Application Priority Data

Sep. 21, 2005    (JP)    ............................. 2005-274017

(51) Int. Cl.
*C12N 9/14*    (2006.01)
*C12N 15/00*    (2006.01)
*C12N 1/20*    (2006.01)
*C12Q 1/00*    (2006.01)
*C12Q 1/34*    (2006.01)
*C12P 21/04*    (2006.01)
*C07H 21/04*    (2006.01)
*C12Q 1/68*    (2006.01)

(52) U.S. Cl. ............................... 435/195; 435/4; 435/6; 435/18; 435/69.1; 435/71.1; 435/252.3; 435/320.1; 435/440; 536/23.2

(58) Field of Classification Search ........................ None
See application file for complete search history.

(56) References Cited

U.S. PATENT DOCUMENTS 6,444,208 B1 *    9/2002    Lonetto et al. ........... 424/185.1

FOREIGN PATENT DOCUMENTS

WO    2004/113498 A2    12/2004

OTHER PUBLICATIONS

Branden et al. Introduction to Protein Structure, Garland Publishing Inc., New York, p. 247, 1991.*
UniProtKB Databases—O58914. 1998. Retrieved from the internet http://www.uniprot.org/uniprot/O58914 on Feb. 1, 2020.*
Supplementary European Search Report mailed October 22, 2008.
K. Gerdes et al., "Prokaryotic Toxin-Antitoxin Stress Response LOCI", Nature Reviews Microbiology, vol. 3, No. 5, pp. 371-382, Apr. 2005.

D.P. Pandey et al., "Toxin-antitoxin loci are highly abundant in free-living but lost from host-associated prokaryotes", Nucleic Acids Research, vol. 33, No. 3, pp. 966-976, 2005.
Kawarabayasi, Y. et al., Part 1 of "Complete sequence and gene organization of the genome of a hyper-thermophilic archaebacterium, Pyrococcus horikoshii OT3", Database NCBI, Accession No. NC_000961.
Kawarabayasi, Y. et al., Part 2 of "Complete sequence and gene organization of the genome of a hyper-thermophilic archaebacterium, Pyrococcus horikoshii OT3", Database NCBI, Accession No. NC_000961.
Kawarabayasi, Y. et al., Part 3 of "Complete sequence and gene organization of the genome of a hyper-thermophilic archaebacterium, Pyrococcus horikoshii OT3", Database NCBI, Accession No. NC_000961.
Kawarabayasi, Y. et al., "Complete sequence and gene organization of the genome of a hyper-thermophilic archaebacterium, Pyrococcus horikoshii OT3 (Supplement)", Database NCBI, Accession No. NC_143082.
Zhang, Y. et al., "Insights into the mRNA Cleavage Mechanism by MazF, an mRNA Interferase", The Journal of Biological Chemistry, vol. 280, No. 5, pp. 3143-3150, Feb. 4, 2005.
K. Gerdes, "Toxin-Antitoxin Modules May Regulate Synthesis of Macromolecules during Nutritional Stress", Journal of Bacteriology, vol. 182, No. 3, pp. 561-572. Feb. 2000.
F. Hayes, "Toxins-Antitoxins: Plasmid Maintenance, Programmed Cell Death, and Cell Cycle Arrest", Science, vol. 301, pp. 1496-1499, Sep. 12, 2003.
Christensen, S.K. et al., "RelE toxins from Bacterial and Archaea cleave mRNAs on translating ribosomes, which are rescued by tmRNA", Molecular Microbiology vol. 48, No. 5, pp. 1389-1400, 2003.
Pedersen, K. et al., "The Bacterial Toxin RelE Displays Codon-Specific Cleavage of mRNAs in the Ribosomal A Site", Cell, vol. 112, pp. 131-140, Jan. 10, 2003.
Christensen, S.K. et al., "Toxin-antitoxin Loci as Stress-response-elements: ChpAK/MazF and ChpBK Cleave Translated RNAs and are Counteracted by tmRNA", Journal of Molecular Biology, vol. 332, pp. 809-819, 2003.
Christensen, S.K. et al., "Overproduction of the Lon protease triggers inhibition of translation in *Escherichia coli*: involvement of the yefM-yoeB toxin-antitoxin system", Molecular Microbiology, vol. 51, No. 6, pp. 1705-1717, 2004.
Zhang, Y. et al., "MazF Cleaves Cellular mRNAs Specifically at ACA to Block Protein Synthesis in *Escherichia coli*", Molecular Cell, vol. 12, pp. 913-923. Oct. 2003.

(Continued)

*Primary Examiner*—Yong D Pak
(74) *Attorney, Agent, or Firm*—Browdy and Neimark, PLLC

(57) ABSTRACT

A novel endoribonuclease activity exhibiting polypeptide; a nucleic acid coding for the polypeptide; a recombinant DNA comprising the nucleic acid; a transformant obtained by transformation using the recombinant DNA; a process for producing the polypeptide, characterized by including the steps of culturing the transformant and collecting the polypeptide from the culture; a process for producing single-strand RNA fragments, characterized by including the step of causing the polypeptide to act on a single-strand RNA; and a method of fragmenting a single-strand RNA.

1 Claim, No Drawings

OTHER PUBLICATIONS

Munoz-Gomez, A. J. et al., "Insights into the specificity of RNA cleavage by the *Escherichia coli* MazF toxin", FEBS Letters, No. 567, pp. 316-320, 2004.

Zhang, J. et al., "Interference of mRNA Function by Sequence-specific Endoribonuclease PemK", The Journal of Biological Chemistry, vol. 279, No. 20, pp. 20678-20684, May 14, 2004.

Mittenhuber, G., Occurence of MazEF-like Antitoxin/Toxin Systems in Bacteria, J. Mol. Microbiol. Biotechnology, vol. 1, No. 2, pp. 295-302, 1999.

Anantharaman, V. et al., "New connections in the prokaryotic toxin-antitoxin network: relationship with the eukaryotic nonsense-mediated RNA decay system", Genome Biology, 4:R81, 2003.

Pandy, D. P. et al., "Toxin-antitoxin loci are highly abundant in free-living but lost from host-associated prokaryotes", Nucleic Acids Research, vol. 33, No. 3, pp. 966-976, 2005.

Yoshida, H., "[2] The Ribonuclease T1 Family", Methods in Enzymology, vol. 341, pp. 28-41, 2001.

* cited by examiner

ENDORIBONUCLEASE

TECHNICAL FIELD

The present invention relates to a novel sequence-specific endoribonuclease which is useful in the field of genetic engineering.

BACKGROUND ART

It has been reported that several prokaryotic plasmids have a post-segregation killing (PSK) function to kill hosts from which the plasmids have been dropped out in order to maintain the plasmids in the hosts. Such plasmids have toxin-antitoxin genes. An antitoxin binds to a toxin in a cell to inactivate the toxin. The antitoxin is labile to degradation by proteases. Degradation of the antitoxin by proteases results in activation of the toxin which is stable (Non-patent Document 1). Such toxin-antitoxin genes also exist on chromosomes of most prokaryotes. They respond to various stresses and have functions in programmed cell death. Although the functions of the toxins have not been fully proven, it has been suggested that CcdB and ParE may control replication targeting DNA gyrase, and RelE and Doc may control transcription (Non-patent Documents 1 and 2).

At least five toxins RelE, ChpAK (MazF), ChpBK, YoeB and YafQ exist in *Escherichia coli* (Non-patent Document 2). Christensen et al. have reported that RelE is an endoribonuclease that recognizes a specific codon of three nucleotides in a ribosome-dependent manner to cleave mRNA (Non-patent Documents 3 and 4). Furthermore, Christensen et al. have reported that ChpAK, ChpBK and YoeB are also endoribonucleases that cleave mRNA in a manner dependent on ribosome and codon (Non-patent Documents 5 and 6).

Inouye et al. have demonstrated that MazF (ChpAK) is an endoribonuclease that recognizes specific nucleotides ACA in a ribosome-independent manner to cleave mRNA (Non-patent Documents 7 and 8). Munoz-Gomez et al. have reported that the cleavage of RNA with mazF is specific for NAC (Non-patent Document 9). Inouye et al. have demonstrated that PemK in a plasmid R100 is an endoribonuclease that recognizes specific nucleotides UAH (H is C, A or U) to cleaves mRNA (Patent Document 1, Non-patent Document 10). As described above, it has been suggested that toxins of the RelE or PemK family may be endoribonucleases that cleave mRNA in a nucleotide-specific manner. In particular, toxins of the PemK family may be endoribonucleases that recognize specific nucleotides in a ribosome-independent manner to cleave mRNA. Many toxins of the PemK family exist in prokaryotes and comparison of their sequences has been studied extensively (Non-patent Documents 1 and 11).

Anantharaman et al. have phylogenetically classified toxins by conducting gene neighborhood analyses on the basis of genetic information about toxins and genetic information about organisms for which genomic analyses have been completed, and predicted toxin-like proteins from proteins of unknown functions (Non-patent Document 12). Furthermore, it has been suggested through the analyses that not only RelE and PemK but also proteins of the Doc family and proteins having PIN domains may have ribonuclease activities. One toxin of the PemK family has been found in *Pyrococcus horikoshii* (Non-patent Document 13).

As to enzymes that cleave nucleic acids in a sequence-specific manner, many restriction enzymes which cleave double-stranded DNA have been found and widely utilized in the field of genetic engineering. As to enzymes that cleave single-stranded RNA in a sequence-specific manner, ribonuclease T1 which specifically cleaves at a G nucleotide has been found and utilized for genetic engineering (Non-patent Document 14). The number of enzymes that recognize plural nucleotides in single-stranded RNA and specifically cleave it is still small. Development of such endoribonucleases has been desired in the field of genetic engineering. If an endoribonuclease that specifically recognizes and cleaves a sequence of three nucleotides (like MazF) or more than three nucleotides is found, it is considered that the endoribonuclease would become a useful enzyme in the field of genetic engineering.

Patent Document 1: WO 2004/113498
Non-patent Document 1: J. Bacteriol., 182:561-572 (2000)
Non-patent Document 2: Science, 301:1496-1499 (2003)
Non-patent Document 3: Molecular Microbiol., 48:1389-1400 (2003)
Non-patent Document 4: Cell, 122:131-140 (2003)
Non-patent Document 5: J. Mol. Biol., 332:809-819 (2003)
Non-patent Document 6: Molecular Microbiol., 51:1705-1717 (2004)
Non-patent Document 7: Molecular Cell, 12:913-920 (2003)
Non-patent Document 8: J. Biol. Chem., 280:3143-3150 (2005)
Non-patent Document 9: FEBS Letters, 567:316-320 (2004)
Non-patent Document 10: J. Biol. Chem., 279:20678-20684 (2004)
Non-patent Document 11: J. Mol. Microbiol. Biotechnol., 1:295-302 (1999)
Non-patent Document 12: Genome Biology, 4:R81 (2003)
Non-patent Document 13: Nucleic Acids Research, 33:966-976 (2005)
Non-patent Document 14: Methods in Enzymology, 341:28-41 (2001)

DISCLOSURE OF INVENTION

Problems to be Solved by the Invention

The present invention has been made in view of the above-mentioned prior art. The main object of the present invention is to find a novel sequence-specific endoribonuclease, to identify the cleavage sequence specificity of the novel sequence-specific endoribonuclease, and to provide its use for genetic engineering.

Means to Solve the Problems

The present inventors have screened for a sequence-specific endoribonuclease and found that a polypeptide encoded by the PH1182 gene in *Pyrococcus horikoshii* is a novel sequence-specific endoribonuclease. Furthermore, the present inventors have identified the cleavage sequence specificity of the enzyme. Thus, the present invention has been completed.

The present invention relates to:

[1] a polypeptide having a sequence-specific endoribonuclease activity, which is represented by the amino acid sequence of SEQ ID NO:1 or an amino acid sequence in which one or more amino acid residue(s) is (are) deleted, added, inserted or substituted in said sequence;

[2] a nucleic acid encoding the polypeptide of [1];

[3] the nucleic acid of [2], which has the nucleotide sequence of SEQ ID NO:2;

[4] a nucleic acid that is capable of hybridizing to the nucleic acid of [2] or [3] under stringent conditions and encodes a poly-peptide having a sequence-specific endoribonuclease activity;

[5] a recombinant DNA containing the nucleic acid of any one of [2] to [4];

[6] a transformant transformed with the recombinant DNA of [5];

[7] a method for producing the polypeptide of [1], the method comprising culturing the transformant of [6] and collecting a polypeptide having a sequence-specific RNA cleavage activity from the culture;

[8] a method for producing a single-stranded RNA degradation product, the method comprising allowing the polypeptide of [1] to act on a single-stranded RNA; and

[9] a method for degrading a single-stranded RNA, the method comprising allowing the polypeptide of [1] to act on a single-stranded RNA.

EFFECTS OF THE INVENTION

The present invention enables finding of a novel sequence-specific endoribonuclease, identification of the cleavage sequence specificity of the novel sequence-specific endoribonuclease, and provision of its use for genetic engineering.

Best Mode for Carrying Out the Invention

1. The Polypeptide of the Present Invention

The polypeptide of the present invention is represented by the amino acid sequence of SEQ ID NO:1 or an amino acid sequence in which one or more amino acid residue(s) is (are) deleted, added, inserted or substituted in said amino acid sequence, and exhibits a sequence-specific endoribonuclease activity.

The activity possessed by the polypeptide of the present invention is an endoribonuclease activity specific for single-stranded RNA. The activity enables hydrolysis of a phosphodiester bond 3' to a ribonucleotide in a single-stranded nucleic acid containing the ribonucleotide as a constituting nucleotide. A nucleic acid hydrolyzed with the above-mentioned activity generates the following: a 3' end having a hydroxyl group and a 5' end having a phosphate group; a 3' end having a phosphate group and a 5' end having a hydroxyl group; or a 5' end having 2',3'-cyclic phosphate and a hydroxyl group.

A nucleic acid having at least one ribonucleotide molecule may be used as a substrate for the polypeptide of the present invention. Examples thereof include, but are not limited to, RNA, RNA containing deoxyribonucleotide(s) and DNA containing ribonucleotide (s). The substrate may contain a nucleotide that is different from ones contained in normal nucleic acids (e.g., deoxyinosine, deoxyuridine or hydroxymethyldeoxyuridine) as long as it does not inhibit the action of the polypeptide of the present invention.

The polypeptide of the present invention acts specifically on a single-stranded nucleic acid. It cannot cleave double-stranded nucleic acids such as a double-stranded RNA or an RNA-DNA hybrid.

The polypeptide of the present invention has an activity of cleaving a nucleic acid in a nucleotide sequence-specific manner. Although it is not intended to limit the present invention, if a sequence 5'-UGG-3', 5'-UUG-3', 5'-UGA-3', 5'-AGG-3' or 5'-AAG-3' exists, it hydrolyzes a phosphodiester bond 3' to the first residue in the sequence. For example, the activity can be confirmed using an oligoribonucleotide DGC001 (SEQ ID NO:7) as a substrate as an activity of hydrolyzing a phosphodiester bond between the 7th and 8th nucleotides in the oligoribonucleotide. The endoribonuclease activity of the polypeptide of the present invention is exhibited in the absence of ribosome. Thus, it is a ribosome-independent activity.

A single-stranded RNA-specific endoribonuclease activity of the polypeptide of the present invention can be measured, for example, using a single-stranded RNA as a substrate. Specifically, the measurement can be carried out by allowing a polypeptide to be subjected to activity measurement to act on a single-stranded RNA, which is transcribed from a DNA as a template using RNA polymerase or chemically synthesized, and determining the presence of RNA cleavage. For example, degradation of RNA can be confirmed using electrophoresis (agarose gel, acrylamide gel, etc.). Attachment of an appropriate label (e.g., radioisotope, fluorescent substance) to the RNA as a substrate facilitates detection of a degradation product following electrophoresis.

The polypeptides of the present invention include a polypeptide represented by an amino acid sequence in which one or more amino acid residue(s) is (are) deleted, added, inserted or substituted in the amino acid sequence of SEQ ID NO:1 as long as the polypeptide exhibits an endoribonuclease activity to hydrolyze single-stranded RNA in a sequence-specific manner. Examples of such mutant polypeptides include a polypeptide having 50% or more, preferably 70% or more, more preferably 90% or more homology to the polypeptide of SEQ ID NO:1. Such a mutant polypeptide is encompassed by the present invention even if it recognizes and cleaves a sequence different from the sequence recognized and cleaved by the polypeptide represented by the amino acid sequence of SEQ ID NO:1.

The polypeptide may have a peptide region that is not indispensable to the activity. For example, a polypeptide having the following being attached is included in the polypeptides of the present invention as long as the polypeptide exhibits a single-stranded RNA-specific RNA cleavage activity: a peptide for increasing translation efficiency; a peptide for facilitating purification of the polypeptide (e.g., histidine tag, glutathione-S-transferase, maltose binding protein); or a protein for increasing expression efficiency (e.g., chaperon).

2. The Nucleic Acid Encoding the Polypeptide of the Present Invention

The present invention provides a nucleic acid encoding a polypeptide having a sequence-specific endoribonuclease activity. Such nucleic acids include, but are not limited to, a nucleic acid encoding a polypeptide having a sequence-specific endoribonuclease activity, which is represented by the amino aced sequence of SEQ ID NO:1 or an amino ace sequence in which one or more, for example one to ten amino acid residue(s) is (are) deleted, added, inserted or substituted in said sequence. Examples of amino acid sequences in which one or more amino acid residue(s) is (are) deleted, added, inserted or substituted in the amino acid sequence of SEQ ID NO:1 include an amino acid sequence having 50% or more, preferably 70% or more, more preferably 90% or more homology to the polypeptide of SEQ ID NO:1.

Furthermore, the nucleic acids of the present invention include a nucleic acid encoding a polypeptide having a sequence-specific endoribonuclease activity that is capable of hybridizing to such a nucleic acid under stringent conditions. The stringent conditions are exemplified by those described in J. Sambrook et al. (eds.), Molecular Cloning: A Laboratory Manual 2nd ed., 1989, Cold Spring Harbor Laboratory. Specifically, under exemplary conditions, incubation with a probe is conducted in 6×SSC containing 0.5% SDS, 5×Denhardt's solution, and 0.01% denatured salmon sperm DNA at 65° C. for 12 to 20 hours. For example, a nucleic acid hybridized with a probe can be detected after removing nonspecifically bound probes by washing in 0.1×SSC containing 0.5% SDS at 37° C.

For example, the nucleic acid encoding the polypeptide of the present invention can be obtained as follows.

A gene having a homology, in terms of the amino acid sequence, to a toxin having an endoribonuclease activity to recognize a specific nucleotide sequence and cleave mRNA (e.g., MazF or PemK) is a candidate for a nucleic acid encoding a polypeptide having a sequence-specific ribonuclease activity. For example, such a candidate gene can be found in a bacterial genome. One toxin of the PemK family has been found in *Pyrococcus horikoshii*.

For example, a candidate gene can be isolated from a bacterial genome by PCR using a primer designed based on nucleotide sequence information. If the entire nucleotide sequence is known, the entire sequence of the candidate gene may be synthesized using a DNA synthesizer.

A protein can be expressed from a candidate gene using an appropriate host (e.g., *Escherichia coli*) transformed with an expression vector having the candidate gene being incorporated. Since expression of a sequence-specific ribonuclease which degrades host RNA can be lethal to the host, it is necessary to strictly suppress the expression of the candidate gene before induction. For example, it is preferable to utilize an expression system such as the pET system (Novagen) which utilizes a promoter for T7 polymerase, or the pCold system (Takara Bio) which is a cold shock expression control system. For conveniently purifying an expression product from a candidate gene, it is advantageous to attach, to the expression product, a peptide for facilitating the purification (e.g., a histidine tag). For this purpose, one containing a region encoding such a peptide may be used as an expression vector.

An endoribonuclease activity can be measured according to the above-mentioned method in which a single-stranded RNA is used as a substrate. A cleavage site can be identified by primer extension using a cleaved RNA as a template, a primer complementary to the RNA and a reverse transcriptase. Since the extension reaction terminates at the cleavage site in the primer extension, the cleavage site can be identified by determining the chain length of the extended strand using electrophoresis. The nucleotide sequence specificity may be identified further strictly by chemically synthesizing oligoribonucleotides having arbitrary sequences, allowing the expression product of the candidate gene to act on them, and determining the presence of cleavage using denaturing acrylamide gel electrophoresis or the like.

3. The Method for Producing the Polypeptide of the Present Invention

For example, the polypeptide of the present invention can be produced by (1) purification from a culture of a microorganism producing the polypeptide of the present invention or (2) purification from a culture of a transformant containing a nucleic acid encoding the polypeptide of the present invention.

Examples of the microorganisms producing the polypeptide of the present invention include, but are not limited to, bacteria of the genus *Pyrococcus*. For example, the polypeptide of the present invention can be obtained from *Pyrococcus horikoshii*, preferably *P. horikoshii* ATCC700860. The microorganism may be cultured under conditions suitable for the growth of the microorganism. The polypeptide of interest produced in the cells or the culture can be purified using a method conventionally used for protein purification such as cell disruption, fractionation by precipitation (e.g., ammonium sulfate precipitation), various chromatographies (ion exchange chromatography, affinity chromatography, hydrophobic chromatography, molecular sieve chromatography) er a combination thereof.

The polypeptide of the present invention can be obtained from a transformant transformed with a recombinant DNA containing a nucleic acid encoding the polypeptide of the present invention. Preferably, an appropriate promoter is operably linked upstream of a polypeptide-encoding nucleic acid in the recombinant DNA. Since the polypeptide of the present invention may exert a lethal action on a host, it is preferable that the promoter or an expression system including the promoter can strictly control the transcription from the nucleic acid encoding the polypeptide of the present invention. The pET system or the pCold system exemplifies such a system.

The recombinant DNA may be transferred as it is into a cell as a host. Alternatively, it may be transferred being inserted into an appropriate vector (e.g., a plasmid vector, a phage vector or a virus vector). The recombinant DNA may be integrated into the host chromosome. There is no specific limitation concerning the host to be transformed. For example, a host conventionally used in the field of recombinant DNA (e.g., *Escherichia coli*, *Bacillus subtilis*, yeast, filamentous fungus, plant, animal, plant culture cell, animal culture cell) may be used.

The polypeptide of the present invention produced from such a transformant can be purified utilizing the above-mentioned purification means. If the nucleic acid encoding the polypeptide of the present invention encodes a polypeptide having a peptide for facilitating purification of the polypeptide being attached, the purification is facilitated very much. A high purity polypeptide can be obtained according to a convenient procedure using a purification means corresponding to the attached peptide (e.g., metal chelate resin for histidine tag, glutathione-immobilized resin for glutathione-S-transferase).

4. Degradation of Single-Stranded RNA Using the Polypeptide of the Present Invention An RNA degradation product can be produced by degrading a single-stranded RNA using the polypeptide of the present invention. Since the polypeptide of the present invention can cleave RNA in a nucleotide sequence-specific manner, the average chain length of the generated RNA degradation products is correlated with the occurrence frequency of the nucleotide sequence recognized by the polypeptide. Thus, the present invention provides an RNA degradation product having certain chain length distribution. Furthermore, it is possible to excise a specific region in RNA utilizing the sequence specificity.

Furthermore, it is possible to selectively degrade a single-stranded RNA using the polypeptide of the present invention. In one embodiment of the present invention, it is possible to inhibit protein synthesis by degrading mRNA in a protein synthesis system (e.g., a cell-free translation system or a transformant) using the polypeptide of the present invention. In this case, if mRNA encoding the protein of interest that has been artificially prepared not to contain a nucleotide sequence recognized by the polypeptide of the present invention is placed in the system, only the mRNA escapes from degradation and the protein of interest is specifically produced in the system. This embodiment is particularly useful for production of a highly pure protein.

EXAMPLES

The following Examples illustrate the present invention in more detail, but are not to be construed to limit the scope thereof.

Among the procedures described herein, basic procedures were carried out as described in J. Sambrook et al. (eds.), Molecular Cloning: A Laboratory Manual 3rd ed., 2001, Cold Spring Harbor Laboratory.

Example 1

Isolation of PH1182 from *P. horikoshii* ATCC700860, and Construction of Expression Plasmid An amino acid sequence of a polypeptide encoded in *P. horikoshii* ATCC700860-derived PH1182 gene and the nucleotide sequence therefor were obtained from NCBI database (accession nos. NP_143082 and NC_000961). A primer PH1182-F (SEQ ID NO:3) and a primer PH1182-R (SEQ ID NO:4) were synthesized for PCR amplification of a DNA region encoding the entire polypeptide based on the information about the nucleotide sequence of PH1182.

*P. horikoshii* ATCC700860 genomic DNA was obtained from ATCC (ATCC No. 700860D). PCR was conducted using Pyrobest DNA polymerase (Takara Bio) as well as 50 ng of the genomic DNA from *P. horikoshii* ATCC700860 and the primers PH1182-F and PH1182-R to obtain a 437-bp amplified DNA fragment. The amplified fragment was digested with restriction enzymes NdeI and XhoI and subjected to agarose gel electrophoresis, and a 416-bp DNA fragment was recovered from the gel.

An expression vector was constructed using pCold TF (Takara Bio). For introducing a termination codon immediately behind the XhoI site at the 3' end of PH1182 gene upon cloning of the gene, pCold TF DNA was digested with restriction enzymes XhoI and XbaI, and a linker composed of two synthetic oligonucleotides STPU1 (SEQ ID NO:5) and STPL2 (SEQ ID NO:6) was inserted thereto by ligation to construct pCold TFb. A recombinant plasmid was obtained by ligating the 416-bp DNA fragment to pCold TFb which had been digested with restriction enzymes NdeI and XhoI. The recombinant plasmid was used to transform *Escherichia coli* JM109. A plasmid was prepared from a colony of a transformant obtained as described above and the nucleotide sequence was confirmed. Then, the plasmid was designated as an expression vector pCold TF-PH1182.

The nucleotide sequence encoding the *P. horikoshii* ATCC700860-derived PH1182 polypeptide inserted in the expression vector pCold TF-PH1182 and the amino acid sequence of the polypeptide are shown in SEQ ID NOS:2 and 1, respectively. In the polypeptide expressed using the expression vector pCold TF-PH1182, a polypeptide consisting of 488 amino acid residues including six histidine residues and a trigger factor polypeptide of 432 amino acid residues is attached to the N terminus of the polypeptide of the amino acid sequence of SEQ ID NO:1. Furthermore, two amino acid residues Leu-Glu are attached at the C terminus.

Example 2

Preparation of *P. horikoshii* ATCC700860-Derived PH1182 Polypeptide

The expression vector pCold TF-PH1182 obtained in Example 1 was used to transform *Escherichia coli* BL21 (DE3) (Novagen) to obtain *Escherichia coli* for expression, pCold TF-PH1182/BL21(DE3). The *Escherichia coli* cell was cultured in 5 ml of LB medium containing 100 µg/ml of ampicillin at 37° C. When OD600 nm reached 0.5, incubation was conducted at 15° C. for 30 minutes, IPTG (Takara Bio) was added at a final concentration of 1 mM to induce expression of the polypeptide, and the cultivation was continued at 15° C. for 24 hours. The cultivation was terminated after 24 hours, and the cells were collected by centrifugation. The cells were suspended in 300 µl of a lysis buffer (50 mM $NaH_2PO_4$, 300 mM NaCl, 10 mM imidazole, pH 8.0), and disrupted using a sonicator (Handy sonic, Tomy) 20 µl of Ni-NTA agarose (Qiagen) was added to a supernatant collected by centrifugation, and the mixture was allowed to stand at 4° C. for 30 minutes. A precipitate collected by centrifugation was washed twice with 100 µl of a washing buffer (50 mM $NaH_2PO_4$, 300 nM NaCl, 20 mM imidazole, pH 8.0). After washing, the precipitate was suspended in 20 µl of an elution buffer (50 mM $NaH_2PO_4$, 300 mM NaCl, 250 mM imidazole, pH 8.0). A supernatant was collected by centrifugation. The same elution procedure was repeated two more times. A total of 60 µl of a sample containing the PH1182 polypeptide was obtained. A portion of the sample was subjected to SDS-PAGE to confirm that the sample contained a polypeptide of the expected size. The concentration of the PH1182 protein in the sample was about 25 ng/µl.

Example 3

Identification of Nucleotide Sequence Specificity of PH1182 Polypeptide Using Oligoribonucleotides as Substrates Oligoribonucleotides were synthesized and cleavage assays were carried out in order to study the nucleotide sequence specificity of a ribonuclease activity of the PH1182 polypeptide obtained in Example 2.

Eleven oligoribonucleotides of SEQ ID NOS:7-17 were synthesized as substrates. A 5-µl reaction mixture consisting of 10 µM of one of the oligoribonucleotides, 5 ng/µl of the PH1182 polypeptide obtained in Example 2 and 10 mM Tris-HCl (pH 7.5) was incubated at 3° C. for 30 minutes. The reaction product was subjected to electrophoresis on 20% denaturing acrylamide gel (20% acrylamide, 7 M urea, 0.5× TBE buffer). After staining with SYBR GREEN II (Takara Bio) the fluorescence image was analyzed using a fluorescence image analyzer FMBIO II Multiview (Takara Bio). Cleavage modes of the respective oligoribonucleotides are shown in Table 1.

Furthermore, the sequence specificity was estimated by comparison of nucleotide sequences surrounding the cleavage sites in view of the presence of cleavage of each oligoribonucleotide. The results are shown in Table 2.

Based on the results, it was shown that the PH1182 polypeptide preferentially recognizes a sequence 5'-UGG-3', 5'-UUG-3', 5'-UGA-3', 5'-AGG-3' or 5'-AAG-3' to hydrolyze a phosphodiester bond 3' to the first residue in the sequence. It was shown that the PH1182 polypeptide is an endoribonuclease having nucleotide sequence specificity quite different from that of MazF.

TABLE 1

| Name | Nucleotide sequence and cleavage site (/ represents cleavage site) | Sequence Identifier | Cleavage PH1182 |
|---|---|---|---|
| DGC001 | GCA/GGUU/GGUUUACAUUAAUU | SEQ ID NO: 7 | + |
| MRI017 | GUU/UGUUAUGUUUCUUA U/GGUUCUU | SEQ ID NO: 8 | + |
| ABC007 | UAU/GAAUAU/GAUCUCAAAUUU | SEQ ID NO: 9 | + |
| MRI023 | AUCUACA/GGGAUCUCCUAUCUACUAU/GGGG | SEQ ID NO: 10 | + |
| MRI002 | AA/AGUCUAAACGCUA/AGCUCUAAAA | SEQ ID NO: 11 | + |
| MRI014 | GGACUCGCCGGAACUCUGCACU/UGA | SEQ ID NO: 12 | + |
| MRI027 | GGGGCUCGCCUUACA/AGCGAU/U/GGG | SEQ ID NO: 13 | + |
| MRI031 | GUGUGUUCCUUUAUU/UGUGUUACUU/U/GGGC | SEQ ID NO: 14 | + |
| ABC001 | GCAGAGUUCAAA/AGCCCUUUU | SEQ ID NO: 15 | + |
| ABC017 | GGAGUCGUAGCUGCAGUAUUU | SEQ ID NO: 16 | − |
| ABC018 | AUACUGCAGCUACGACUCCUU | SEQ ID NO: 17 | − |

TABLE 2

| Name | Nucleotide sequence | Cleavage PH1182 |
|---|---|---|
| DGC001 (1) | U U/G G | + |
| MRI017 (1) | A U/G G | + |
| MRI023 (1) | A U/G G | + |
| MRI027 (1) | U/U G G | + |
| MRI031 (1) | U/U G G | + |
| MRI017 (2) | U U/U G | + |
| MRI014 (1) | C U/U G | + |
| MRI031 (2) | U U/U G | + |
| ABC007 (1) | A U/G A | + |
| ABC007 (2) | A U/G A | + |
| DGC001 (2) | C A/G G | + |
| MRI023 (2) | C A/G G | + |
| MRI002 (1) | A A/A G | + |
| MRI002 (2) | U A/A G | + |
| MRI027 (2) | C A/A G | + |
| ABC001 (1) | A A/A G | + |
| MRI014 (2) | C C G G | − |
| MRI027 (3) | G G G G | − |
| MRI017 (3) | U A U G | − |
| ABC018 (1) | A C U G | − |
| MRI031 (3) | U G U G | − |
| MRI014 (3) | C U C G | − |
| ABC017 (1) | G U A G | − |
| ABC017 (2) | C U G C | − |
| MRI017 (4) | A U G U | − |
| ABC007 (3) | A U U U | − |
| MRI017 (5) | U U U C | − |
| MRI017 (6) | C U U A | − |
| ABC018 (2) | A C G A | − |
| MRI014 (4) | C G G A | − |
| ABC001 (2) | C A G A | − |
| ABC018 (3) | G C A G | − |
| ABC017 (3) | G G A G | − |
| MRI002 (3) | U A A A | − |
| ABC007 (4) | A A A U | − |
| MRI002 (4) | A A A C | − |
| MRI002 (5) | A A C G | − |

Cleavage site: Cleavage site is represented by /.

INDUSTRIAL APPLICABILITY

The present invention provides a novel sequence-specific endoribonuclease. Since the enzyme can recognize and cleave a specific sequence in RNA, it is useful for analysis of RNA molecules, preparation of RNA fragments, control of cells (e.g., inhibition of protein synthesis) through cleavage of intracellular RNA, and the like.

Sequence Listing Free Text

SEQ ID NO:3; PCR primer PH1182-F to amplify a DNA fragment encoding PH1182 protein.

SEQ ID NO:4; PCR primer PH1182-R to amplify a DNA fragment encoding PH1182 protein.

SEQ ID NO:5; Oligonucleotide STPU1 to modify pCold TF.

SEQ ID NO:6; Oligonucleotide STPL2 to modify pCold TF.

SEQ ID NO:7; Oligoribonucleotide DGC001.

SEQ ID NO:8; Oligoribonucleotide MRI017.

SEQ ID NO:9; Oligoribonucleotide ABC007.

SEQ ID NO:10; Oligoribonucleotide MRI023.

SEQ ID NO:11; Oligoribonucleotide MRI002.

SEQ ID NO:12; Oligoribonucleotide MRI014.

SEQ ID NO:13; Oligoribonucleotide MRI027.

SEQ ID NO:14; Oligoribonucleotide MRI031.

SEQ ID NO:15; Oligoribonucleotide ABC001.

SEQ ID NO:16; Oligoribonucleotide ABC017.

SEQ ID NO:17; Oligoribonucleotide ABC018.

The invention claimed is:

1. A method for degrading a single-stranded RNA, the method comprising:
allowing a polypeptide having an endoribonuclease activity specific for single-stranded RNA which cleaves RNA in a nucleotide sequence-specific manner to act on a single-stranded RNA,
wherein said polypeptide has the amino acid sequence of SEQ ID NO: 1 or an amino acid sequence having 90% or more homology to the polypeptide of SEQ ID NO: 1.

* * * * *

UNITED STATES PATENT AND TRADEMARK OFFICE
CERTIFICATE OF CORRECTION

| | | |
|---|---|---|
| PATENT NO. | : 7,745,190 B2 | |
| APPLICATION NO. | : 12/067769 | |
| DATED | : June 29, 2010 | |
| INVENTOR(S) | : Shimada | |

It is certified that error appears in the above-identified patent and that said Letters Patent is hereby corrected as shown below:

Title Page,

At section (75) Inventors, correct the misspelled inventor's name by deleting "Kiyoza Asada" and insert --Kiyozo Asada--.

Signed and Sealed this
Fourth Day of October, 2011

David J. Kappos
*Director of the United States Patent and Trademark Office*

```
                        SEQUENCE LISTING

<160> NUMBER OF SEQ ID NOS: 17

<210> SEQ ID NO 1
<211> LENGTH: 138
<212> TYPE: PRT
<213> ORGANISM: Pyrococcus horikoshii ATCC 700860

<400> SEQUENCE: 1

Met Pro Lys Gln Gly Glu Ile Trp Thr Ala Pro Phe Pro Tyr Phe
  1               5                  10                  15

Asp Asp Arg Gly Lys Leu Thr Phe Lys Ile Arg Pro Ile Leu Ile
                 20                  25                  30

Val Ser Asn Asp Glu Phe Asn Asp Asn Ala Leu Asp Val Ile Ile
                 35                  40                  45

Cys Gln Ile Ser Arg Phe Glu Tyr Glu Arg Ile Leu Lys Leu Pro
                 50                  55                  60

Ser Lys Met Arg Ser Lys Ile Lys Ile Ile Thr Asn Asn Asp Leu
                 65                  70                  75

Asp Pro Asn Thr Ser Gly Lys Leu Arg Asn Ile Ser Ile Ile Lys
                 80                  85                  90

Pro Tyr Lys Leu Phe Ser Ile Ser Lys Asp Lys Leu Asn Asn Tyr
                 95                 100                 105

Lys Phe Ile Gly Lys Leu Lys Pro Lys Ala Met Ser Glu Ile Ser
                110                 115                 120

Leu Val Leu Lys Glu Val Phe Gln Thr Glu Asn Ile Ser Ser Gln
                125                 130                 135

Asp Thr Pro

<210> SEQ ID NO 2
<211> LENGTH: 414
<212> TYPE: DNA
<213> ORGANISM: Pyrococcus horikoshii ATCC 700860

<400> SEQUENCE: 2
atgcctaaac aaggtgaaat ctggacagca cccttcccat attttgatga ccgcggaaag      60
ttaacattca aaataagacc aatcctcata gtatccaacg atgaattcaa cgacaacgca     120
ctagatgtta atctgtca  aatctccaga tttgaatatg aaagaatcct aaagctccct     180
tctaaaatgc ggagcaaaat taaataata  acaaacaacg accttgatcc aaacaccagc     240
ggtaaactac gaaatataag tataattaaa ccttacaagc ttttctccat ctcaaaagat     300
aaacttaaca actacaagtt cattggaaaa ttaaagccaa aagctatgag tgaaataagc     360
```
ctagtcctaa aagaagtatt ccaaacagaa aatatatcct cacaagacac ccct        414

<210> SEQ ID NO 3
<211> LENGTH: 36
<212> TYPE: DNA
<213> ORGANISM: Artificial
<220> FEATURE:
<223> OTHER INFORMATION: PCR primer PH1182-F to amplify a DNA fragment
      encoding PH1182 protein.

<400> SEQUENCE: 3
ggggagctaa catatgccta aacaaggtga aatctg        36

<210> SEQ ID NO 4
<211> LENGTH: 30
<212> TYPE: DNA
<213> ORGANISM: Artificial
<220> FEATURE:
<223> OTHER INFORMATION: PCR primer PH1182-R to amplify a DNA fragment
      encoding PH1182 protein.

<400> SEQUENCE: 4
ggggctcgag aggggtgtct tgtgaggata        30

<210> SEQ ID NO 5
<211> LENGTH: 12
<212> TYPE: DNA
<213> ORGANISM: Artificial
<220> FEATURE:
<223> OTHER INFORMATION: Oligonucleotide STPU1 to modify pCold TF.

<400> SEQUENCE: 5
tcgagtaact aa        12

<210> SEQ ID NO 6
<211> LENGTH: 12
<212> TYPE: DNA
<213> ORGANISM: Artificial
<220> FEATURE:
<223> OTHER INFORMATION: Oligonucleotide STPL2 to modify pCold TF.

<400> SEQUENCE: 6
ctagttagtt ac        12

<210> SEQ ID NO 7
<211> LENGTH: 21
<212> TYPE: RNA
<213> ORGANISM: Artificial
<220> FEATURE:
<223> OTHER INFORMATION: Oligoribonucleotide DGC001.

<400> SEQUENCE: 7
gcagguuggu uuacauuaau u        21

<210> SEQ ID NO 8
<211> LENGTH: 25
<212> TYPE: RNA
<213> ORGANISM: Artificial
<220> FEATURE:
<223> OTHER INFORMATION: Oligoribonucleotide MRI017.

<400> SEQUENCE: 8 guuguuaug uucuuaugg uucuu        25

<210> SEQ ID NO 9
<211> LENGTH: 21

```
<212> TYPE: RNA
<213> ORGANISM: Artificial
<220> FEATURE:
<223> OTHER INFORMATION: Oligoribonucleotide ABC007.

<400> SEQUENCE: 9
uaugaauaug aucucaaauu u                                           21

<210> SEQ ID NO 10
<211> LENGTH: 30
<212> TYPE: RNA
<213> ORGANISM: Artificial
<220> FEATURE:
<223> OTHER INFORMATION: Oligoribonucleotide MRI023.

<400> SEQUENCE: 10
aucuacaggg aucccuauc uacuaugggg                                   30

<210> SEQ ID NO 11
<211> LENGTH: 25
<212> TYPE: RNA
<213> ORGANISM: Artificial
<220> FEATURE:
<223> OTHER INFORMATION: Oligoribonucleotide MRI002.

<400> SEQUENCE: 11
aaagucuaaa cgcuaagcuc uaaaa                                       25

<210> SEQ ID NO 12
<211> LENGTH: 25
<212> TYPE: RNA
<213> ORGANISM: Artificial
<220> FEATURE:
<223> OTHER INFORMATION: Oligoribonucleotide MRI014.

<400> SEQUENCE: 12
ggacucgccg gaacucugca cuuga                                       25

<210> SEQ ID NO 13
<211> LENGTH: 25
<212> TYPE: RNA
<213> ORGANISM: Artificial
<220> FEATURE:
<223> OTHER INFORMATION: Oligoribonucleotide MRI027.

<400> SEQUENCE: 13
ggggcucgcc uuacaagcga uuggg                                       25

<210> SEQ ID NO 14
<211> LENGTH: 30
<212> TYPE: RNA
<213> ORGANISM: Artificial
<220> FEATURE:
<223> OTHER INFORMATION: Oligoribonucleotide MRI031.

<400> SEQUENCE: 14
guguguuccu uuauuugugu uacuuugggc                                  30

<210> SEQ ID NO 15
<211> LENGTH: 21
<212> TYPE: RNA
<213> ORGANISM: Artificial
<220> FEATURE:
<223> OTHER INFORMATION: Oligoribonucleotide ABC001.

<400> SEQUENCE: 15
```

```
gcagaguuca aaagcccuuu u                                      21

<210> SEQ ID NO 16
<211> LENGTH: 21
<212> TYPE: RNA
<213> ORGANISM: Artificial
<220> FEATURE:
<223> OTHER INFORMATION: Oligoribonucleotide ABC017.

<400> SEQUENCE: 16
ggagucguag cugcaguauu u                                      21

<210> SEQ ID NO 17
<211> LENGTH: 21
<212> TYPE: RNA
<213> ORGANISM: Artificial
<220> FEATURE:
<223> OTHER INFORMATION: Oligoribonucleotide ABC018

<400> SEQUENCE: 17
auacugcagc uacgacuccu u                                      21
```